United States Patent
Marker

(12) 
(10) Patent No.: US 6,303,839 B1
(45) Date of Patent: *Oct. 16, 2001

(54) PROCESS FOR PRODUCING POLYMER GRADE OLEFINS

(75) Inventor: Terry L. Marker, Palos Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/593,187

(22) Filed: Jun. 14, 2000

(51) Int. Cl.[7] ................ C07C 1/10; C07C 4/06
(52) U.S. Cl. ............ 585/313; 585/312; 585/311; 585/314; 585/315; 585/324; 585/328; 585/329; 585/330; 585/639; 585/648; 585/653
(58) Field of Search .................. 585/313, 312, 585/311, 314, 315, 324, 328, 329, 330, 639, 648, 653

(56) References Cited

U.S. PATENT DOCUMENTS

| | | | |
|---|---|---|---|
| 3,723,562 | 3/1973 | Heckelsberg | 260/683 D |
| 3,928,483 | 12/1975 | Chang et al. | 260/668 R |
| 4,025,575 | 5/1977 | Chang et al. | 260/682 |
| 4,252,479 | 2/1981 | Scherfenberg | 406/182 |
| 4,447,669 | 5/1984 | Hamon et al. | 585/640 |
| 4,496,786 | 1/1985 | Santilli et al. | 585/640 |
| 4,499,314 | 2/1985 | Seddon et al. | 585/408 |
| 4,547,616 | 10/1985 | Avidan et al. | 585/640 |
| 4,590,174 | 5/1986 | Kukes et al. | 502/219 |
| 4,677,242 | 6/1987 | Kaiser | 585/638 |
| 4,677,243 | 6/1987 | Kaiser | 585/638 |
| 4,843,183 | 6/1989 | Inui | 585/640 |
| 4,861,938 | 8/1989 | Lewis et al. | 585/640 |
| 4,873,390 | 10/1989 | Lewis et al. | 585/638 |
| 4,973,792 | 11/1990 | Lewis et al. | 585/638 |
| 5,026,935 | 6/1991 | Leyshon et al. | 585/315 |
| 5,095,163 | 3/1992 | Barger | 585/640 |
| 5,126,308 | 6/1992 | Barger et al. | 502/214 |
| 5,191,141 | 3/1993 | Barger et al. | 585/640 |
| 5,447,622 | 9/1995 | Kerby et al. | 208/78 |
| 5,475,173 | 12/1995 | Cheung et al. | 585/259 |
| 5,914,433 | * 6/1999 | Marker | 585/313 |
| 6,023,005 | 2/2000 | Lattner et al. | 585/639 |

FOREIGN PATENT DOCUMENTS

| | | |
|---|---|---|
| 1 219 882 | 3/1987 | (CA) . |
| WO 93/13013 | 7/1993 | (WO) . |

OTHER PUBLICATIONS

Article "Structure–Reactivity Relationships in Methanol to Olefin Conversion on Various Microporous Crystalline Catalysts" by T. Inui, included in *Structure–Activity and Selectivity Relationships in Heterogeneous Catalysis*, edited by R.K. Grasselli and A.W. Sleight, Elsevier Science Publishers B.V., Amsterdam, 1991, pp. 233–242.

* cited by examiner

Primary Examiner—Hien Tran
Assistant Examiner—Thuan D. Dang
(74) Attorney, Agent, or Firm—John G. Tolomei; Frank S. Molinaro; Richard P. Silverman

(57) ABSTRACT

The present invention relates to a process for the production of light olefins comprising olefins having from 2 to 4 carbon atoms per molecule from an oxygenate feedstock. The process comprises passing the oxygenate feedstock to an oxygenate conversion zone containing a metal aluminophosphate catalyst to produce a light olefin stream. A propylene stream and/or mixed butylene is fractionated from said light olefin stream and cracked to enhance the yield of ethylene and propylene products. This combination of light olefin product and propylene and butylene cracking in a riser cracking zone or a separate cracking zone provides flexibility to the process which overcomes the equilibrium limitations of the aluminophosphate catalyst. In addition, the invention provides the advantage of extended catalyst life and greater catalyst stability in the oxygenate conversion zone.

7 Claims, 3 Drawing Sheets

PROCESS FOR PRODUCING POLYMER GRADE OLEFINS

FIELD OF THE INVENTION

This invention relates to a process for the production of light olefins from an oxygenate feedstream.

BACKGROUND OF THE INVENTION

Light olefins have traditionally been produced through the process of steam or catalytic cracking. Because of the limited availability and high cost of petroleum sources, the cost of producing light olefins from such petroleum sources has been steadily increasing. Light olefins serve as feeds for the production of numerous chemicals. As the emerging economies of the Third World strain toward growth and expansion, the demand for light olefins will increase dramatically.

The search for alternative materials for light olefin production has led to the use of oxygenates such as alcohols and, more particularly, to the use of methanol, ethanol, and higher alcohols or their derivatives. These alcohols may be produced by fermentation or from synthesis gas. Synthesis gas can be produced from natural gas, petroleum liquids, and carbonaceous materials including coal, recycled plastics, municipal wastes, or any organic material. Thus, alcohol and alcohol derivatives may provide non-petroleum based routes for the production of olefin and other related hydrocarbons.

Molecular sieves such as the microporous crystalline zeolite and non-zeolitic catalysts, particularly silicoaluminophospbates (SAPO), are known to promote the conversion of oxygenates to hydrocarbon mixtures. Numerous patents describe this process for various types of these catalysts: U.S. Pat. Nos. 3,928,483; 4,025,575; 4,252,479; 4,496,786; 4,547,616; 4,677,243; 4,843,183; 4,499,314; 4,447,669; 5,095,163; 5,191,141; 5,126,308; 4,973,792; and 4,861,938.

The process may be generally conducted in the presence of one or more diluents which may be present in the oxygenate feed in an amount between about 1 and about 99 molar percent, based on the total number of moles of all feed and diluent components fed to the reaction zone (or catalyst). Diluents include—but are not limited to—helium, argon, nitrogen, carbon monoxide, carbon dioxide, hydrogen, water, paraffins, hydrocarbons (such as methane and the like), aromatic compounds, or mixtures thereof. U.S. Pat Nos. 4,861,938 and 4,677,242 particularly emphasize the use of a diluent combined with the feed to the reaction zone to maintain sufficient catalyst selectivity toward the production of light olefin products, particularly ethylene. The above U.S. patents are hereby incorporated by reference.

U.S. Pat. No. 5,026,935 discloses a process for the preparation of ethylene from $C_4$ or higher feed by the combination of cracking and metathesis to form ethylene and propylene and at least a portion of the propylene is metathesized to ethylene. U.S. Pat. No. 4,590,174 discloses an olefin metathesis process employing a catalyst comprising an inorganic refractory oxide support containing at least one of tungsten oxide and molybdenum oxide and a promoting agent for the disproportionation reaction. Example 3 of U.S. Pat. No. 3,723,562 describes the conversion of propylene to a mixture of ethylene and butenes using a $WO_3$-$SiO_2$ catalyst containing about 8 weight percent tungsten oxide. Conditions used were 800° F., 100 psig and 15 $hr^{-1}$ WHSV. Propylene conversion was 19 percent with 37.6 percent selectivity to ethylene and 62.4 percent selectivity to butenes. U.S. Pat. No. 3,723,562 is hereby incorporated by reference.

CA-1,219,882 discloses a process for the production of 1-butene from $C_4$ hydrocarbon mixtures containing 2-butene. The $C_4$ hydrocarbon mixture is isomerized in a reaction zone to 1-butene in the presence of an acid catalyst. The isomerization zone effluent is distilled to recover a hydrogen offgas, a 1-butene side-draw product, and 2-butene in a bottom stream. The bottom stream is recycled to the isomerization zone for the further isomerization of the 2-butene to 1-butene. The process is operated in the absence of steam without significant cracking or skeletal isomerization.

International Patent Application No. 93/13013 to Kvisle et al. relates to an improved method for producing a silicon-alumino-phosphate catalyst which is more stable to deactivation by coking. The patent discloses that after a period of time, all such catalysts used to convert methanol to olefin (MTO) lose the active ability to convert methanol to hydrocarbons primarily because the microporous crystal structure is coked; that is, filled up with low volatility carbonaceous compounds which block the pore structure. The carbonaceous compounds can be removed by conventional methods such as combustion in air. In a paper by T. Inui titled "Structure-Reactivity Relationships in Methanol to Olefins Conversion on Various Microporous Crystalline Catalysts," which was included in *Structure-Activity and Selectivity Relationships in Heterogeneous Catalysis*, edited by R. K. Grasselli and A. W. Sleight, Elsevier Science Publishers B.V., Amsterdam, 1991, on pages 233–242, Inui discloses the highest reported ratio of ethylene/propylene produced from methanol over a SAPO-34 catalyst as about 15:1 (see FIG. 4, page 240).

Generally, the ratio of ethylene/propylene on a carbon basis varies from about 0.1 to about 10 and, more typically, varies from about 0.8 to about 2.5. Furthermore, ethylene and propylene yields are reduced by the production of heavier hydrocarbons such as $C_4$ and $C_5$ olefins. This narrow band limits the flexibility of the process and the value of the net products produced. Methods are sought to alter the product distribution of the MTO process for making light olefins to provide processing flexibility and overcome the equilibrium limitations of aluminophosphate catalyst of the MTO process. Methods are sought to reduce the production of $C_4$ and $C_5$ olefins from the MTO process relative to the production of ethylene and propylene. These and other disadvantages of the prior art are overcome by the present invention, and a new improved process for conversion of oxygenates to hydrocarbons is provided.

SUMMARY OF THE INVENTION

In the present invention, a combination of a light olefin production process and a catalytic cracking process is employed to improve the amount of desirable olefin products above the equilibrium amount provided by a molecular sieve catalyst. It was discovered that the use of this combination of an aliphatic hetero compound conversion process in a first reaction zone and a secondary reaction zone, operating at an effective temperature which is elevated relative to the temperature of the first reaction zone, improved the overall yield of light olefins beyond the limitations of the molecular sieve catalyst. By operating at conditions which are favorable for the ethylene and propylene production, the yields of butylene and heavier hydrocarbons can be reduced in favor of the more profitable and desirable ethylene and propylene products and the catalyst life and stability of the aluminophosphate catalyst in the oxygenate conversion zone can be improved. Preferably, the ratio of butylene and heavier to propylene from a combination of oxygenation conversion and cracking is reduced to less than about 0.30 on a weight basis, and more preferably, the yield of butylene and heavier to propylene is reduced to less than about 0.15 on a weight basis.

The invention provides a process for the production of light olefins comprising ethylene and propylene from an oxygenate feedstock such as an alcohol or an ether. The process comprises passing an oxygenate feedstock to a fluidized reaction zone in the presence of a diluent, the feedstock having from 1 to 4 carbon atoms per molecule. The first or fluidized reaction zone contains an aluminophosphate molecular sieve catalyst at conditions effective to convert the oxygenate feedstock to a light olefin product stream comprising olefins comprising ethylene, propylene and butylene and to produce a spent aluminophosphate molecular sieve catalyst. The light olefin product stream is passed to a separation zone to separate the light olefin product stream into an ethylene stream, a propylene stream, and a mixed butylene and heavier stream. At least a portion of the spent aluminophosphate molecular sieve catalyst is withdrawn from the fluidized reaction zone, and the spent aluminophosphate molecular sieve catalyst is passed to a regenerator to regenerate the spent aluminophosphate molecular sieve catalyst with an oxygen-containing stream to produce a regenerated catalyst. A first portion of the regenerated catalyst is returned to the fluidized reaction zone and a second portion of the regenerated catalyst is admixed with a portion of the mixed butylene and heavier stream to provide a feed admixture, and the feed admixture is passed to a secondary reaction zone at conditions effective to convert the mixed butylene and heavier stream to produce a second product stream comprising additional amounts of ethylene and propylene and to produce a third regenerated catalyst. At least a portion of the second product stream is passed to the fluidized reaction zone.

In a further embodiment, the present invention comprises a process for the production of light olefins comprising ethylene from a feedstock comprising methanol. The process comprises passing the feedstock in the presence of a diluent to a first reaction zone containing an aluminophosphate catalyst at conditions effective to convert at least a portion of the feedstock to form a first reactor effluent stream comprising ethylene, propylene, and butylene and heavier olefins. The first reactor stream and a second reactor effluent are passed to a $C_2$ fractionation zone to provide an ethylene product stream and a $C_3$ and heavier stream. The $C_3$ and heavier stream is passed to a $C_3$ fractionation zone to provide a propylene stream and a mixed butylene and heavier stream. At least a portion of the mixed butylene and heavier stream is cracked in a secondary cracking zone to provide the second reactor effluent stream, and the second reactor effluent stream is returned to the $C_2$ fractionation zone.

In an alternate embodiment, a portion of the mixed butylene and heavier stream is passed to a polymerization zone at conditions effective to produce a polymer gasoline stream comprising $C_3$–$C_6$ hydrocarbons. A portion of the polymer gasoline stream is passed to the secondary cracking zone to produce additional amounts of ethylene and propylene. In a still further embodiment, a portion of the propylene is passed to the polymerization zone for the production of the polymer gasoline stream.

In a still further embodiment, the present invention relates to a process for producing light olefins. The process comprises admixing a feedstream comprising an alcohol or an ether having 1 to 4 carbon atoms per molecule with a catalyst recirculation stream to provide a feedstream/ recirculation stream. The feedstream/recirculation stream is passed to a fluidized reaction zone containing an aluminophosphate molecular sieve catalyst in the presence of a diluent at effective conditions to produce a light olefin product stream comprising ethylene, propylene, and heavier olefins and a spent catalyst having a carbon deposit thereon. The light olefin product stream is passed to a separation zone to produce an ethylene stream, a propylene stream, and a mixed $C_4$-plus stream. A portion of the spent catalyst is withdrawn from the fluidized reaction zone and passing the portion of the spent catalyst to a regeneration zone and therein contacting the spent catalyst with an oxygen-containing stream at effective regeneration conditions to produce a regenerated catalyst comprising less than about 1 weight percent carbon. A feed admixture comprising at least a portion of the $C_4$-plus stream and at least a portion of the regenerated catalyst is passed to a riser reactor in fluid communication with the fluidized reaction zone at effective cracking conditions to at least partially crack the feed admixture to produce a second product stream comprising additional amounts of ethylene and propylene and the regenerated catalyst is at least partially carbonized to provide a partially coked catalyst comprising from about 2 to about 30 weight percent carbon. The second product stream and the partially coked catalyst are passed to the fluidized reaction zone.

DETAILED DESCRIPTION OF THE INVENTION

Figure 1:
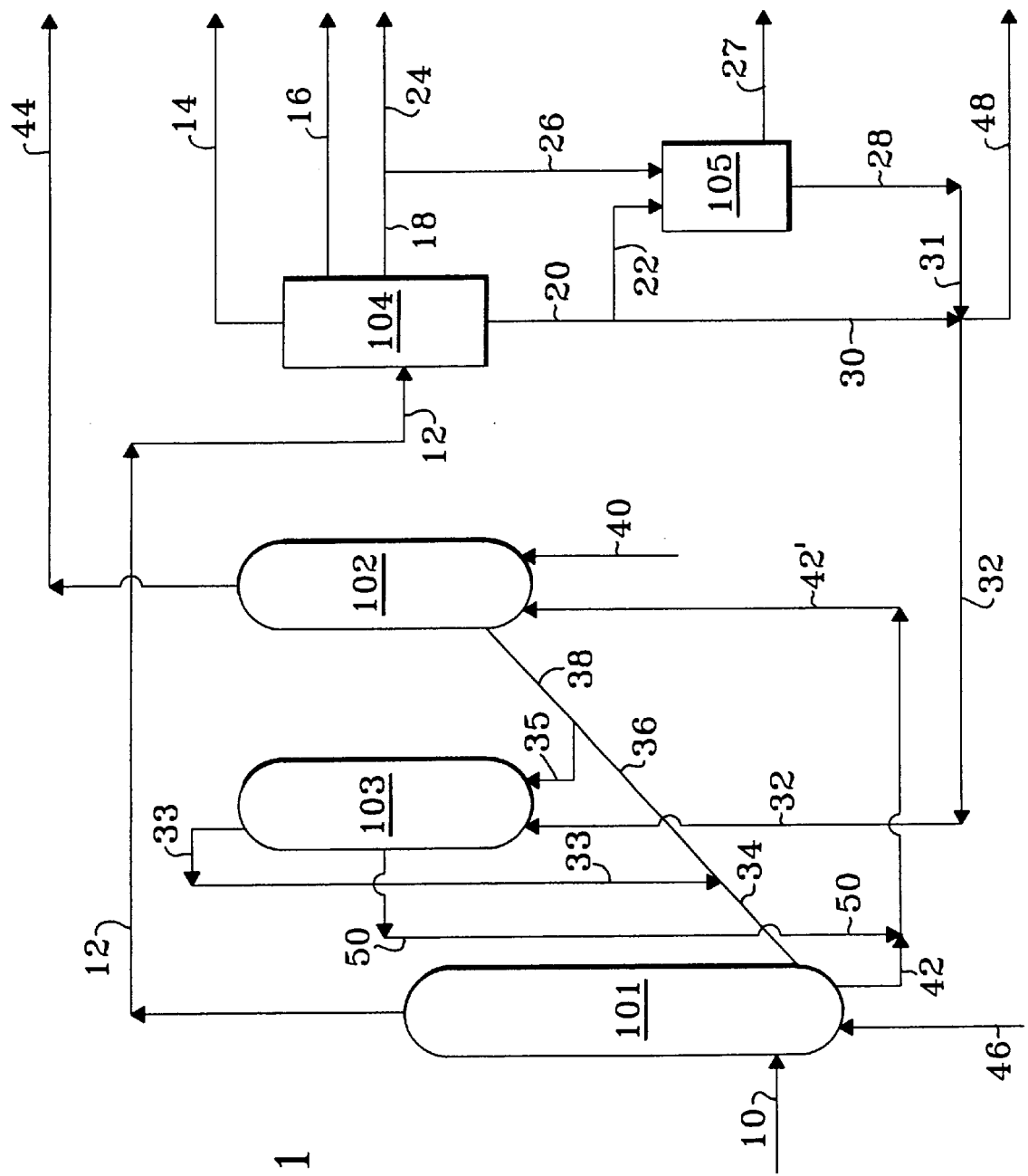
FIG. 1 is a schematic process flow diagram illustrating the process of the instant invention.

This invention comprises a process for the catalytic conversion of a feedstock comprising one or more aliphatic hetero compounds comprising alcohols, halides, mercaptans, sulfides, amines, ethers, and carbonyl compounds or mixtures thereof to a hydrocarbon product containing light olefinic products, i.e., $C_2$, $C_3$ and/or $C_4$ olefins. The feedstock is contacted with a silicoaluminophosphate molecular sieve at effective process conditions to produce light olefins. Silicoaluminophosphate molecular sieves which produce light olefins are generally employable in the instant process. The preferred silicoaluminophosphates are those described in U.S. Pat. No. 4,440,871. Silicoaluminophosphate molecular sieves employable in the instant process are more fully described hereinafter.

The instant process employs an oxygenate feedstock. The term "oxygenate feedstock" is employed herein to include alcohols, ethers, and carbonyl compounds (aldehydes, ketones, carboxylic acids, and the like). The oxygenate feedstock preferably contains from 1 to about 10 carbon atoms and, more preferably, contains from 1 to about 4 carbon atoms. Suitable reactants include lower straight or branched chain alkanols, their unsaturated counterparts. Representatives of suitable oxygenate compounds include methanol, dimethyl ether, ethanol, diethyl ether, methylethyl ether, formaldehyde, dimethyl ketone, acetic acid, and mixtures thereof.

In accordance with the process of the present invention, an oxygenate feedstock is catalytically converted to hydrocarbons containing aliphatic moieties such as—but not limited to—methane, ethane, ethylene, propane, propylene, butylene, and limited amounts of other higher aliphatics by contacting the aliphatic hetero compound feedstock with a preselected catalyst. The term "aliphatic compound feedstock", as employed in the present invention and described herein, designates only the organic material used as the feed. The total charge of feed to the aliphatic conversion reaction zone may contain additional compounds such as diluents. The term "oxygenate" as employed in the present invention and described herein designates compounds such as alcohols, ethers, aldehydes, ketones, and mixtures thereof. The invention will be herein discussed further with reference to oxygenates and an oxygenate conversion process which are the more preferred embodiments of the invention.

A diluent is required to maintain the selectivity of the catalyst to produce light olefins, particularly ethylene and propylene. Examples of diluents which may be used are helium, argon, nitrogen, carbon monoxide, carbon dioxide, hydrogen, steam, paraffinic hydrocarbons (e.g., methane), aromatic hydrocarbons (e.g., benzene and toluene), and mixtures thereof. The amount of diluent used can vary considerably and is usually from about 5 to about 90 mole percent of the feedstock and preferably from about 25 to about 75 mole percent. The use of steam as the diluent provides certain equipment cost and thermal efficiency advantages. The phase change between steam and liquid water can be employed to advantage in transferring heat between the feedstock and the reactor effluent, and the separation of the diluent from the product requires simple condensation of the water to separate the water from the hydrocarbons. Ratios of 1 mole of feed to about 0.1–5 moles of water have been disclosed.

The oxygenate conversion process of the present invention is preferably conducted in the vapor phase such that the oxygenate feedstock is contacted in a vapor phase in a reaction zone with a molecular sieve catalyst at effective process conditions to produce hydrocarbons, i.e., an effective temperature, pressure, WHSV and, optionally, an effective amount of diluent, correlated to produce hydrocarbons. The process is affected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected. The feedstock flow rate affects olefin production. Increasing the feedstock flow rate (expressed as weight hourly space velocity, or WHSV) enhances the formation of olefin production relative to paraffin production. However, the enhanced olefin production relative to paraffin production is offset by a diminished conversion of oxygenate to hydrocarbons.

The oxygenate conversion process is effectively carried out over a wide range of pressures, including autogenous pressures. At pressures between about 0.001 atmospheres (0.76 torr) and about 1000 atmospheres (760,000 torr), the formation of light olefin products will be affected although the optimum amount of product will not necessarily form at all pressures. The preferred pressure is between about 0.01 atmospheres (7.6 torr) and about 100 atmospheres (76,000 torr). More preferably, the pressure will range from about 1 to about 10 atmospheres. The pressures referred to herein for the process are exclusive of the inert diluent, if any, that is present and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range and beyond, the selectivities, conversions and/or rates to light olefin products may not occur at the optimum, although light olefin such as ethylene may still be formed.

The temperature which may be employed in the oxygenate conversion process may vary over a wide range depending, at least in part, on the selected molecular sieve catalyst. In general, the process can be conducted at an effective temperature between about 200° and about 700° C. Temperatures outside the stated range are not excluded, although they do not fall within certain desirable embodiments of the present invention. At the lower end of the temperature range, and thus, generally at a lower rate of reaction, the formation of the desired light olefin products may become markedly slow. At the upper end of the temperature range and beyond, the process may not form an optimum amount of light olefin products and catalyst deactivation may be rapid. Notwithstanding these factors, the reaction will still occur and the feedstock, at least in part, can be converted to the desired light olefin products at temperatures outside the range between about 200° and about 700° C.

In the oxygenate conversion process wherein aliphatic hetero compounds are converted into light olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane, and most preferably, by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 Angstroms. The average effective diameter of the pores of preferred catalysts is determined by measurements described in D. W. Breck, *Zeolite Molecular Sieves* by John Wiley & Sons, New York (1974), hereby incorporated by reference in its entirety. The term "effective diameter" is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves, and non-zeolitic molecular sieves.

Zeolitic molecular sieves in the calcined form may be represented by the general formula:

$$Me_{2/n}O:Al_2O_3:xSiO_2:yH_2O$$

where Me is a cation, x has a value from about 2 to infinity, n is the cation valence, and y has a value of from about 2 to 10.

Typically well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11, and MCM-22. Other zeolites include those having a high silica content, i.e., those having silica/alumina ratios greater than 10 and typically greater than 100 can also be used. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above-identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the element mixture present. Preferred elements (EL) are silicon, magnesium, and cobalt with silicon being especially preferred.

The preparation of various ELAPOs are well known in the art and may be found in U.S. Pat. No. 5,191,141 (ELAPO); U.S. Pat. No. 4,554,143 (FeAPO); U.S. Pat. No. 4,440,871 (SAPO); U.S. Pat. No. 4,853,197 (MAPO, MnAPO, ZnAPO, CoAPO); U.S. Pat. No. 4,793,984 (CAPO), U.S. Pat. No. 4,752,651; and U.S. Pat. No. 4,310,440; all of which are incorporated by reference. Generally, the ELAPO molecular sieves are synthesized by hydrothermal crystallization from a reaction mixture containing reactive sources of EL, aluminum, phosphorus, and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

A preferred embodiment of the invention is one in which the element (EL) content varies from about 0.005 to about 0.05 mole fraction. If EL is more than one element, then the total concentration of all the elements is between about 0.005 and 0.05 mole fraction. An especially preferred embodiment is one in which EL is silicon (usually referred to as SAPO). The SAPOs which can be used in the instant invention are any of those described in U.S. Pat. Nos. 4,440,871; 5,126,308, and 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 angstroms. Another SAPO, SAPO-17, as exemplified in Examples 25 and 26 of the '871 patent, is also preferred. The SAPO-17 structure is characterized in that it adsorbs oxygen, hexane, and water but does not adsorb isobutane, indicating that it has a pore opening of greater than about 4.3 angstroms and less than about 5.0 angstroms.

The preferred oxygenate conversion catalyst may be, and preferably is, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Such matrix materials are often, to some extent, porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the non-zeolitic and/or zeolitic molecular sieves preferably comprise about 1 to 99 percent, more preferably about 5 to about 90 percent and still more preferably about 10 to about 80 percent, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke, is deposited on the catalyst. The carbonaceous deposit material has the effect of reducing the number of active sites on the catalyst which thereby affects the extent of the conversion. During the conversion process a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 weight percent, or only partially regenerate the catalyst, e.g. to from about 2 to 30 weight percent carbon. Preferably, the regenerated catalyst will contain about 0 to 20 percent and more preferably from about 0 to 10 percent carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. The details concerning the conditions for regeneration are known to those skilled in the art and need not be further disclosed herein.

It was discovered that the butene and heavier material produced in the oxygenate conversion zone and following separation from the first reaction zone effluent can be converted in a secondary conversion zone to produce additional amounts of ethylene and propylene. It is believed that simply passing a portion of the reactor effluent which comprises methanol to the secondary reaction zone at a higher temperature will not achieve the benefits of the instant invention because the presence of methanol, a polar compound, will inhibit cracking reaction by tying up acid sites on the catalyst. Furthermore, it was surprisingly found that the secondary conversion zone wherein the butene and heavier material is contacted with a catalyst at conditions effective to convert at least a portion of the butene and heavier materials to ethylene and propylene favored the production of propylene rather than the smaller molecule, ethane. The catalyst found to produce this conversion was the same catalyst employed in the oxygenate conversion zone. The effective conditions at which the additional ethylene and propylene were produced when the butene and heavier were contacted with the catalyst comprised a secondary reaction temperature above about 460° C. Preferably, the secondary reaction temperature comprises a temperature between about 460° and about 700° C., and more preferably, the secondary reaction temperature is between about 460° and about 700° C., and most preferably, the secondary reaction temperature is between about 580° and about 650° C. Conversion of the butene produced in the oxygenate conversion was evaluated by measuring the conversion and the selectivity for the production of ethylene in a fixed bed reactor. The fixed bed reactor contained a SAPO-34 catalyst. It was found that conversion of 2-butene at temperatures ranging between 460° and 580° C. resulted in the production of primarily propylene and heavier olefins and initially produced ethylene at a 20 percent selectivity at short residence times. It was discovered that by increasing reactor temperature over 460° C. and diluting the olefin feed with a nitrogen diluent, the product distribution was shifted toward light olefins. Dilution of the feed with a diluent such as steam appeared to have the same effect on product distribution as dilution with nitrogen. Separate tests with a spray dried catalyst comprising 40 percent SAPO-34, 40 percent kaolin clay, and 20 percent Si-Al binder gave the same results as the 100 percent SAPO-34 powder.

The conversion of butylene and heavier material can be accomplished by separating this product fraction from the oxygenate conversion zone effluent and contacting the butylene and heavier fraction with the catalyst from the first reaction zone immediately following regeneration. Ideally, this conversion will take place in a secondary reaction zone between the regeneration zone and the first reaction zone and the catalyst and the cracked lighter products (ethylene and propylene) will be transferred to the first reaction zone. To effect the cracking reaction favoring light olefins, the secondary reaction zone may be a riser cracking reaction zone with a short residence time to minimize hydrogen transfer reactions which would favor production of paraffins such as ethane and propane. The cracking reactions can also be carried out in a separate fluidized bed containing the oxygenate conversion catalyst. With a separate fluidized bed, the catalyst circulation can be controlled to flow to and from the regenerator at effective catalyst circulation rates which favor the production of ethylene and propylene in the secondary reaction zone and minimize production of the paraffins and methane. When a separate fluidized bed reaction zone is employed as the secondary reaction zone, a product gas stream comprising the cracked products is passed to the oxygenate conversion zone or first reaction zone and catalyst withdrawn from the secondary reaction zone is returned to the regenerator. Because the cracking reaction is a slightly endothermic reaction, some heat of the cracking reaction is provided by the regenerated catalyst. However, an optional butene and heavier preheater may be required to vaporize the feed to the secondary reaction zone when the catalyst circulation rates are very low such as a catalyst/oil ( mixed butylene and heavier stream) ratio between about 1 and about 20, In the second reaction zone, preferably the catalyst/oil ratio is less than about 20, and more preferably in the second reaction zone, the catalyst/oil ratio is less than about 10. It is believed that the reaction in the secondary reaction zone over the SAPO catalyst proceeds initially by polymerizing some of the butylene and heavier hydrocarbons in addition to the cracking reactions which, at an effective temperature, favors the production of propylene while also producing ethylene.

In order to maximize the amount of ethylene and propylene and to minimize the production of methane produced from the butylene and heavier stream, it is desired to minimize the presence of diolefins in the feed to the secondary reaction zone. Diolefin conversion to monoolefin hydrocarbons may be accomplished with a conventional selective hydrogenation process such as disclosed in U.S. Pat. No. 4,695,560 hereby incorporated by reference.

A portion of the butylene and heavier stream, when cracked, will be converted to paraffinic compounds such as methane, ethane, propane, and heavier hydrocarbons. Unless at least a portion of these compounds is removed, they will build up in the system and reduce the overall efficiency of the process. Therefore, a drag stream comprising $C_4$ and heavier hydrocarbons is removed from the process and used for plant fuel or blended into other hydrocarbon products such as motor gasoline.

The specified combination of the conversion of the feedstock to a mixture of light olefins at conditions favoring the production of these components coupled with the use of the thus formed butylene and heavier olefins to produce further quantities of product ethylene and propylene provides a synergistic combination of oxygenate conversion and cracking reaction steps whereby there are obtained substantially improved overall yields of the desired light olefins: ethylene and propylene.

DETAILED DESCRIPTION OF THE DRAWINGS

The following description of the present process is made with reference to the drawings. In the interest of simplifying the description of the invention, the process system in the drawing does not contain the several conduits, valves, heat exchangers, and the like which—in actual practice—would be provided in accordance with routine skill in the art to enable the process to be carried out on a continuous basis.

FIG. 1 illustrates the operation of the instant invention. An oxygenate feedstock in line 10 comprising an alcohol or an ether having about 1 to about 4 carbon atoms per molecule is passed to a fluidized reaction zone 101. In the fluidized reaction zone, the oxygenate feedstock contacts an alumino phosphate catalyst in the presence of a diluent which is shown as being introduced via line 46. The fluidized reaction zone is operated at a fluid reaction pressure and a fluid reaction temperature which is effective to convert the oxygenate feedstock to produce a light olefin product stream which is withdrawn in line 12 and passed to a separation zone 104. In the separation zone 104, the light olefin product stream is separated by fractionation to provide a fuel gas stream in line 14, an ethylene stream in line 16, a propylene stream in line 18, and a mixed butylene and heavier stream in line 20. As the reaction takes place in the fluidized reaction zone, a portion of the catalyst is deactivated by the build-up of coke on the catalyst to produce a spent catalyst. A portion of the spent catalyst is conveyed to a regenerator 102 via catalyst transfer lines 42 and 42'. In the regenerator 102 the spent catalyst is contacted with an oxygen-containing stream such as air or oxygen introduced in line 40 to at least partially reduce the build-up of coke on the spent catalyst and to produce a regenerated catalyst having a reduced amount of coke relative to spent catalyst. During the regeneration, carbon oxides are produced which are removed from the regeneration zone via line 44. Preferably, spent catalyst comprises from about 3 to about 15 weight percent coke and the regenerated catalyst comprise about 1 to about 5 weight percent coke. A first portion of the regenerated catalyst is returned to the fluidized reaction zone 101 via lines 38, 36, and 34. A second portion of the regenerated catalyst is passed to a secondary reaction zone 103 via catalyst transfer lines 38 and 35. At least a portion of the mixed butylene and heavier stream is passed to the secondary reaction zone via lines 20, 30, and 32. In the secondary reaction zone 103, at conditions effective for the conversion, the mixed butylene and heavier stream is converted or cracked to provide to a second product stream comprising additional amounts of ethylene and propylene. Preferably, the secondary reaction zone is maintained at a secondary reactor temperature of between about 480° and about 700° C. and a pressure ranging from about 100 kPa (15 psia) to about 450 kPa (65 psia) to obtain the desired conversion of the mixed butylene. More preferably, the secondary reaction zone temperature ranges between about 550° and about 650° C. The riser reaction may be carried out in the presence of a second diluent such as steam, nitrogen, methane, etc. The second product stream and regenerated catalyst are withdrawn from the regenerator 103 and passed to the fluidized reaction zone 101 via transfer lines 33 and 34. A propylene product stream is withdrawn via lines 18 and 24. The secondary reaction zone 103 may be a riser cracking zone wherein all of the effluent and catalyst from the riser are passed to the first reaction zone; or the secondary reaction zone may be a fluidized bed to which flows regenerated catalyst in line 35 and from which catalyst is returned to the regenerator 102 via lines 50 and 42'. When the secondary reaction zone 103 is a separate fluidized bed, the vapor portion of the effluent from the secondary reaction zone is passed via line 33 to the first reaction zone via lines 33 and 34. This use of a separate fluidized bed for the secondary reaction zone provides improved control of the catalyst/oil ratio in the secondary zone. In an alternative embodiment, a portion of the propylene product in line 18 is passed to a polymerization zone 105 via line 26 to produce a polymer gasoline stream in line 28. The polymer gasoline stream is passed to the secondary reaction zone via lines 28, 31, and 32 wherein the polymer gasoline is converted to additional amounts of ethylene and propylene. It is believed that the conversion of the polymer gasoline will be more selective to the production of ethylene and produce less methane than the direct conversion of propylene. In a further embodiment, a portion of the mixed butylene and heavier stream in line 20 may be passed to the polymerization zone either separately via line 22 or admixed with the propylene to produce the polymer gasoline in line 28. In the polymerization of the propylene product stream, any propane present in the propylene product stream may be more easily separated from the polymer gasoline than from the propylene and there is less incentive to separate the propane in separation zone 104. A drag stream in line 48 comprising paraffins is withdrawn in line 48 to remove unconverted hydrocarbons including $C_{1-C_6}$ paraffins which are not easily converted in the secondary reaction zone.

Figure 2:
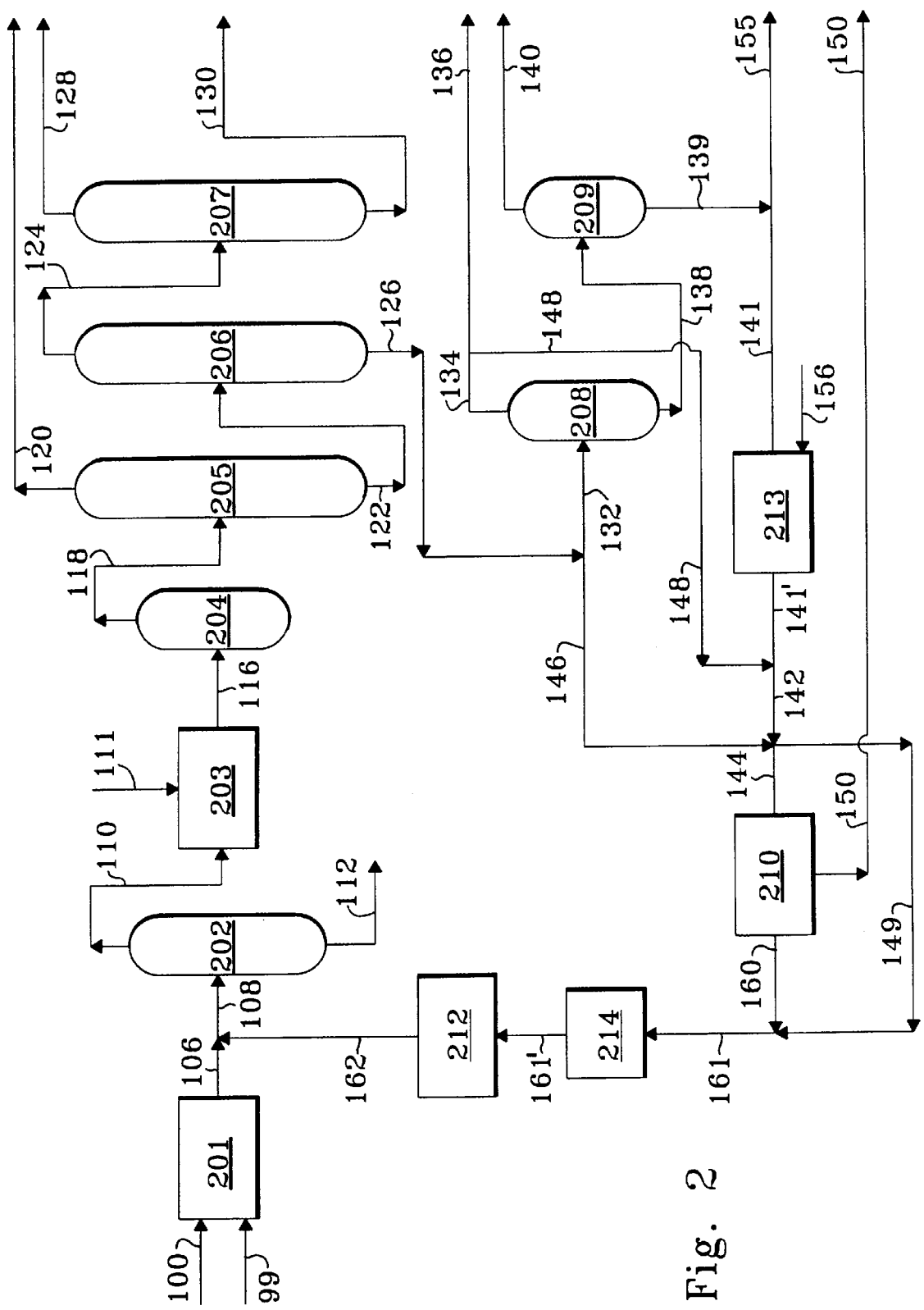
FIG. 2 is a schematic process flow diagram illustrating the conversion of mixed butenes or propylene in a polymerization zone and returning the polymerized gasoline to a cracking reaction zone.

FIG. 2 shows an alternate operation of the instant invention wherein a separate cracking zone is employed to increase the overall yield of ethylene relative to propylene and butylene. Referring to FIG. 2, an oxygenate feedstock is passed to a fluidized reaction zone 201 via line 100 in the presence of a diluent introduced in line 99. The fluidized reaction zone contains an oxygenate conversion catalyst selected from the group consisting of SAPO-17, SAPO-34, and mixtures thereof. The fluidized reaction zone 201 is operated at conditions effective to produce a light olefin reactor product stream in line 106 comprising ethylene, propylene, mixed butylenes, carbon dioxide, and water. The light olefins reactor product stream in line 106 is passed via lines 106 and 108 to a water removal zone 202 to remove water in line 112 and to produce a dewatered reactor product stream in line 110. The dewatered reactor product stream is passed via line 110 to a $CO_2$ removal zone 203 wherein the dewatered reactor product stream is contacted with a caustic wash in line 111 to remove the carbon dioxide and produce a caustic treated reactor product stream in line 116. The caustic treated reactor product stream is passed via line 116 to a dryer zone 204 containing a solid adsorbent selected from the group consisting of zeolite molecular sieves, activated carbon, silica gel, activated alumina, and mixtures thereof to reduce the water content of the caustic treated reactor product stream to less than about 5 ppm-wt water as a dried reactor product stream in line 118. The dried reactor product stream in line 118 is passed to a demethanizer zone 205 to separate methane and lighter compounds from the dried reactor product stream and to produce a fuel gas stream in line 120 and a demethanized stream in line 122. The demethanized stream in line 122 is passed to a deethanizer zone 206 to provide a $C_2$ stream in line 124 and a $C_3^+$ and heavier stream in line 126. The $C_2$ stream is passed to an ethylene column 207 to separate an ethylene product stream in line 128 from an ethane stream in line 130. The purity of the ethylene product stream preferably ranges from about 95 to about 99.9 volume percent ethylene. The $C_3$ and heavier stream is passed via lines 126 and 132 to a propylene column 208 to separate a propylene stream 134 from a propane plus stream comprising propane and mixed butenes and heavier in line 138. The propane plus stream in line 138 is passed to a depropanizer column 209 to provide a propane stream in line 140 and a mixed butene and heavier stream comprising olefinic and diolefinic hydrocarbons in line 139. In accordance with the present invention, a portion of the mixed butylene and heavier stream in line 139 is passed via lines 139 and 141 to a selective hydrogenation zone 213 wherein the mixed butene and heavier stream is contacted with a selective catalyst and a hydrogen stream in line 156, in the conventional manner, to selectively convert diolefin hydrocarbons to monoolefinic hydrocarbons which are withdrawn in line 141' and passed to a secondary reaction zone 212 via lines 141', 142, 149, 161, 161', and optional preheater 214. The optional preheater 214 provides additional heat of reaction to the secondary reaction zone 212 as required to provide a vaporized feed to the secondary reaction zone 212. In the secondary reaction zone 212, the mixed butylenes and heavier stream are converted to additional amounts of ethylene and propylene. The secondary reaction zone is operated at effective conditions to convert $C_3$–$C_6$ olefinic hydrocarbons to produce a second reactor effluent stream in line 162 comprising ethylene and propylene. The second reactor effluent stream in line 162 is combined with the effluent from the fluidized reaction zone in line 106 as described with reference to FIG. 1.

In an alternate operation, a portion of the propylene product stream in line 134 is passed to the secondary reaction zone 212 via lines 134, 148, 142, 149, 161, 161', and the optional preheater. Thus, either mixed butylenes and heavier or propylene or mixtures thereof are passed to the cracking reaction zone 212. In a further embodiment, the mixed butylenes and heavier and/or the propylene or mixtures thereof are polymerized in a polymerization zone 210 to produce a polymerized gasoline stream 160 which is passed to the cracking reaction zone 212 via lines 160, 161, 161', and the optional preheater. Polymerization of the butylenes and propylene to heavier molecules followed by cracking favors the production of ethylene which raises the overall ethylene production from the complex. A portion of the propylene product is passed to the polymerization zone 210 via lines 134, 148, 142, 141, and 144. The mixed butylene and heavier stream is passed to the polymerization zone 210, following selective hydrogenation in the selective hydrogenation zone 213 is passed via lines 141', 142, and 144. A portion of the polymerization gasoline in line 162 is withdrawn from the polymerization zone 212 and passed to the secondary reaction zone 212 via lines 160, 161, 161' and preheater 214. Another portion of the polymerization gasoline produced in the polymerization zone 210 is withdrawn in line 150 for sale or for use in gasoline blending as a motor fuel blending component. As required a drag stream comprising unconverted $C_1$–$C_6$ paraffins is withdrawn in line 155. Preferably, the drag stream comprises between about 1 to about 15 volume percent of the butylene and heavier stream 139.

Figure 3:
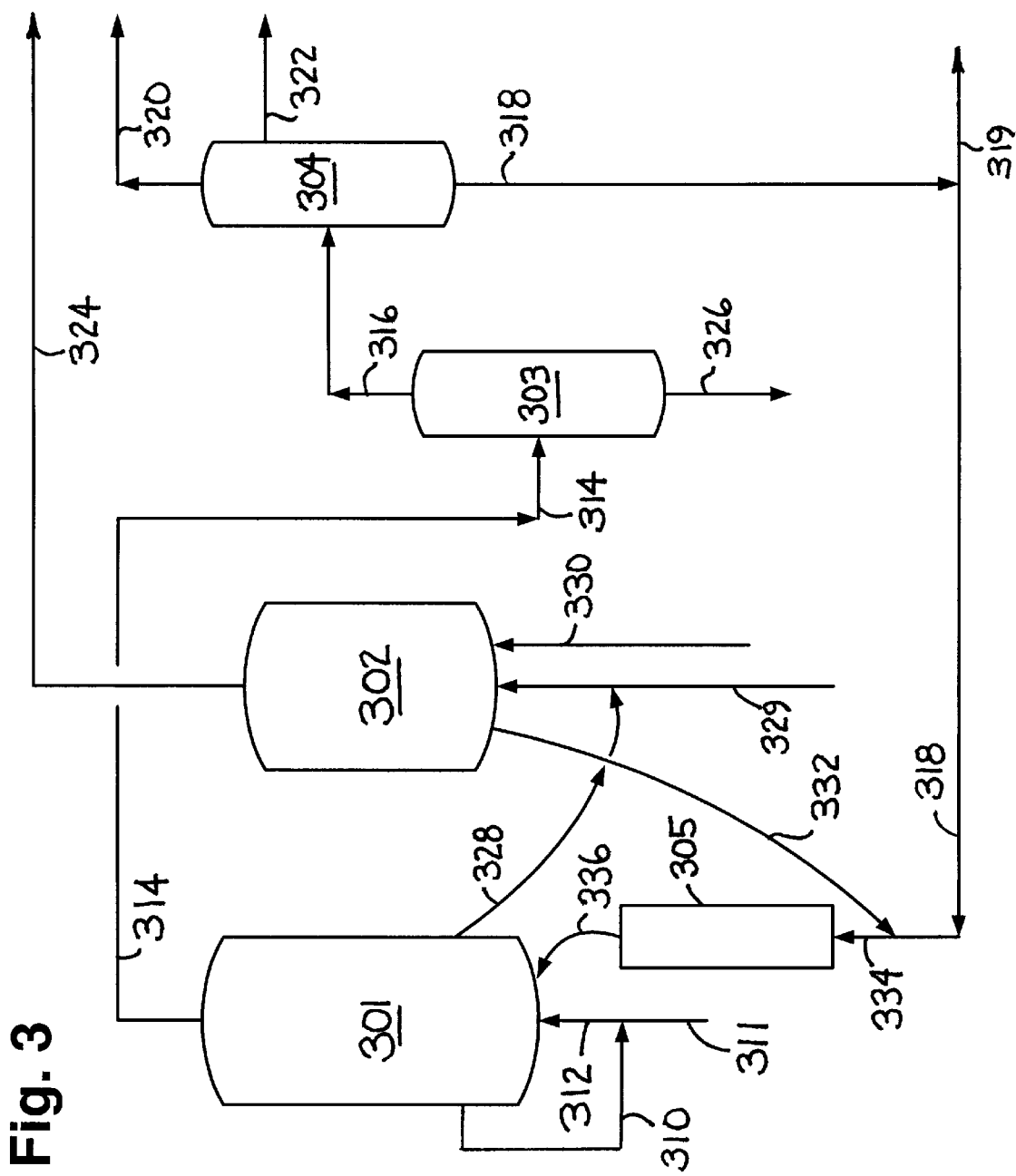
FIG. 3 is a schematic process flow diagram showing the integration of the riser cracking zone.

FIG. 3 shows an example of the instant invention wherein a riser cracking zone for the conversion of butene and heavier hydrocarbons is integrated with a fluidized reaction zone for the production of ethylene and propylene from an oxygenate feedstock. The oxygenate feedstock in line 311 is passed to a fluidized reaction zone 301 via lines 311 and 312 in the presence of a diluent which is admixed with a recirculation catalyst stream in line 310 prior to being introduced to the fluidized reaction zone 301. The fluidized reaction zone contains an aluminophosphate catalyst, or more specifically, a SAPO catalyst such as SAPO-34 or SAPO-17 or mixtures thereof and is operated at effective conditions to produce a light olefin reactor product stream in line 314. The light olefin reactor product stream comprises ethylene, propylene, mixed butylenes, and heavier. Carbon dioxide and water are also present in the light olefin reactor product stream. The light olefin reactor product stream is withdrawn in line 314 and passed to a quench tower, or water removal zone 303, wherein the light olefin reactor product stream is cooled to condense water and produce a dewatered product stream in line 316 and a water stream in line 326. The water stream in line 326 may also comprise unreacted oxygenate and catalyst fines. The water removal zone 303 may include conventional heat removal techniques to recover heat from the light olefin reactor product stream for use at other points in the process. The dewatered product stream in line 316 is passed to a product separation zone 304 for the conventional separation of the dewatered product stream into an ethylene product stream in line 320, a propylene stream in line 232, and a $C_4$-plus stream or butylene and heavier stream in line 318.

In the operation of the fluidized reaction zone 301, as the reaction proceeds, a portion of the catalyst becomes spent by a buildup of carbon deposits and reduces the amount of active catalyst in the fluidized reaction zone. A portion of the spent catalyst must be regenerated to maintain activity and selectivity to produce light olefins in the fluidized reaction zone 301. Therefore, a portion of the spent catalyst is removed from the fluidized reaction zone 301 via line 328 and admixed with a lift gas stream such as steam or nitrogen in line 329 to convey the spent catalyst to a regeneration zone 302 in a conventional manner. In the regeneration zone 302, the spent catalyst is oxidized in the presence of an oxygen-containing stream, introduced via line 330. A combustion effluent stream comprising carbon oxides is withdrawn in line 324 and a regenerated catalyst stream is removed in line 332. Preferably, the regenerated catalyst stream contains between 0 and about 1 weight percent carbon. More preferably, the regenerated catalyst stream contains less than about 0.5 weight percent carbon. According to the present invention, essentially all of the regenerated catalyst stream in line 332 is admixed with a portion of the $C_4$-plus stream comprising butylene and heavier hydrocarbons in line 318 to provide a butylene/catalyst feed mixture in line 334 and at effective cracking conditions, the butylene/catalyst feed admixture in line 334 is passed to a secondary riser cracking zone 305 to at least partially crack the butylene and heavier hydrocarbons to produce additional amounts of ethylene and propylene. To prevent the buildup of $C_1$–$C_6$ paraffins in the secondary riser cracking zone 305, a portion of the butylene and heavier stream in line 318 is removed as a drag stream in line 319 and used as fuel or returned to a syngas plant as feed. A riser effluent stream comprising light olefins and partially coked catalyst in line 336 is withdrawn from the secondary riser cracking zone 305 and passed to the fluidized reaction zone 301. Preferably, the partially coked catalyst comprises between about 2 to about 30 weight percent coke. More preferably, the partially coked catalyst contains between 2 and 10 weight percent coke. In this manner, the carbon content and hence the activity of the fluidized reaction zone 301 is maintained while increasing the overall conversion of ethylene and propylene.

The following examples are only used to illustrate the present invention and are not meant to be limiting.

EXAMPLES

Example I

Three oxygenate conversion pilot plant runs were conducted using a spray-dried metal aluminophosphate catalyst comprising 40 percent SAPO-34, 40 percent kaolin clay, and 20 percent Si-Al binder. The catalyst was loaded into a 2.2 cm (7/8 inch) ID porcelain-lined, stainless steel reactor and placed in a three-zone bronze block furnace. The reactor was heated to 435° C. for Run A, 455 ° C. for Run B, and 475° C. for Run C under an $N_2$ purge at 138 kPa (5 psig). This condition was held for 1 hour to pretreat the catalyst. The $N_2$ flow was stopped and a methanol/water mixture (80/20 by weight) was introduced at 1 $hr^{-1}$ MeOH WHSV and continued until the reactor effluent contained greater than 50 percent MeOH and DME. Table 1 summarizes the time on-stream and product selectivities at the point where the overall conversion was 99 percent for each run. It can be seen that increasing reaction temperature increases the ethylene/propylene product ratio, but increasing reaction temperature decreases the catalyst life.

TABLE 1

Summary of Oxygenate Conversion Selectivities for
SAPO-34 with Increasing Reactor Temperature

| RUN | A | B | C |
| --- | --- | --- | --- |
| Inlet Temp (° C.) | 435 | 455 | 475 |
| Pressure (kPa) | 138 | 138 | 138 |
| MeOH WHSV ($hr^{-1}$) | 1.0 | 1.0 | 1.0 |
| Catalyst Life (hr at >99% Conv) | 4.3 | 3.3 | 2.3 |
| Selectivities at 99% Conversion (mole %) | | | |
| $C_1$ | 3.3 | 4.7 | 7.7 |
| $C_2$ | 0.6 | 0.6 | 0.8 |
| $C_2^=$ | 50.3 | 52.4 | 53.7 |
| $C_3$ | 0.4 | 0.4 | 0.5 |
| $C_3^=$ | 33.5 | 30.8 | 27.0 |
| $C_4$S | 9.0 | 7.9 | 6.9 |

TABLE 1-continued

Summary of Oxygenate Conversion Selectivities for
SAPO-34 with Increasing Reactor Temperature

| RUN | A | B | C |
|---|---|---|---|
| $C_{5+}S$ | 2.0 | 3.1 | 3.2 |
| $C_2^=/C_3^=$ Ratio | 1.50 | 1.70 | 1.99 |

Example II

The conversion of butenes over an aluminophosphate catalyst was evaluated with a catalyst containing about 40 weight percent SAPO-34 and a binder for a series of reactor temperatures to simulate riser reactor operation in a fixed bed reactor. Approximately 20 g of catalyst were loaded into a 2.2 cm (7/8 inch) ID porcelain-lined, stainless steel reactor and placed in a 3-zone bronze block furnace. The reactor was heated to temperatures between 460° and 580° C. and purged with nitrogen for approximately 1 hour to precondition the catalyst. The nitrogen flow was stopped and 2-butene was introduced at a rate of about 0.5 $hr^{-1}$ WHSV on catalyst for a period of about 5 hours.

According to the above procedure, the reactor was filled with the SAPO-34-containing catalyst and was heated to a temperature of 460° C. Following 1 hour of purging with nitrogen, vaporized 2-butene was introduced to the reactor at a rate of about 0.5 WHSV on catalyst. The conversion of the 2-butene gradually decreased from an initial value of 66 percent to a value near the end of the run of about 44 percent at about 4.5 hours on-stream. The selectivity to ethylene began at about 7 percent and decreased to about 6 percent over the same period. The selectivity to propylene began at about 25 percent and increased to about 30 percent over the same period.

Example III

The procedure of Example III was repeated at a reactor temperature of about 580° C. At 580° C., the initial $C_4$ conversion was 75 percent and decreased more rapidly than in Example II, reaching a value of about 30 percent after about 4.5 hours on-stream. The selectivity to ethylene initially was about 20 percent and decreased to about 8 percent after about 4.5 hours on-stream. The selectivity to methane initially was about 10 percent and increased to about 17 percent after about 4.5 hours on-stream. The selectivity to propylene initially was about 35 percent and decreased to about 32 percent after about 4.5 hours on-stream.

Example IV

The procedure of Example III was repeated at a reactor temperature of about 580° C. and after heating and purging the reactor with nitrogen for about 1 hour, the 2-butene vapor was introduced at about 75 percent dilution with nitrogen. The conversion of $C_4$'s was about 70 percent initially and decreased to about 5 percent after about 4.5 hours on-stream. The selectivity to ethylene initially was about 22 percent and decreased to about 12 percent after about 4.5 hours on-stream. The selectivity to methane initially was about 3 percent and increased to about 12 percent after about 4.5 hours on-stream. The selectivity to propylene was 55 percent initially and decreased to about 45 percent after about 4.5 hours on-stream.

Example V

A simulated MTO complex processing about 600 MM metric tons per annum of methanol is operated conventionally over a SAPO-34 catalyst in a fluidized reactor to produce either a maximum amount of propylene (Case MP), or the maximum amount of ethylene (Case ME) by the appropriate selection of process variables. The resulting yields on a weight basis in kg/hr are shown in Table 2. For the same methanol feed rate, the maximum ethylene case produces about 36.6 weight percent more ethylene than the maximum propylene case, and the maximum propylene case produces about 50 weight percent more propylene than the maximum ethylene case. When the additional processing step cracking of a portion of the $C_4$ plus olefins, that is, butylenes, and $C_5$ and $C_6$ olefins, according to the present invention is added to the maximum propylene case, the resulting material balance is shown as Case MPC. The yields for the cracking cases are based on the experimental results presented in Examples II–IV. In Case MPC, the weight ratio of the total ethylene and propylene production to the total $C_4$ plus olefin yield increases from about 4.5 to about 22.5, while the weight ratio of the ethylene to propylene decreases from about 0.75 to about 0.69. The ratio of butylene and heavier decreases from about 0.39 to about 0.07. Similarly, when the C4 cracking step is added to the maximum case (Case ME), the net yields are shown in Table 2 as Case MEC. In Case MEC, the weight ratio of the total ethylene and propylene production to the total production of C4 plus olefins increases from about 5.34 to about 19.7 and the weight ratio of ethylene to propylene decreases from about 1.54 to about 1.34. The ratio of butylene and heavier to propylene decreases from about 0.48 to about 0.12. With respect to the key light olefin products, ethylene and propylene($C_2+C_3$), in the maximum propylene cases, the ethylene yield increases by about 10 weight percent and the propylene yield increases by about 19.7 weight percent. In the maximum ethylene case, the effect of C4 plus cracking increases the propylene yield by about 5.4 weight percent and increases the propylene yield by about 21.6 weight percent. The coke production in Case MPC increases about 46 weight percent over Case MP, and the coke production in Case MEC increases about 12 weight percent over Case ME. Thus, the addition of the $C_4$ plus olefin cracking step significantly increases the production of ethylene and propylene relative to the $C_4$ plus olefins, and surprisingly favors the production of propylene relative to the production of ethylene.

TABLE 2

Material Balances for Maximum Ethylene and Maximum Propylene Cases

| | Feed kg/hr | Case MP kg/hr | Case MPC kg/hr | Case ME kg/hr | Case MEC kg/hr |
|---|---|---|---|---|---|
| Methanol | 74274 | | | | |
| Water | 18568 | 60327 | 60327 | 60327 | 60327 |
| Methane | | 186 | 339 | 1117 | 1227 |
| Ethane | | 137 | 137 | 206 | 206 |
| Ethylene | | 11017 | 12129 | 15048 | 15861 |
| Propane | | 169 | 216 | 169 | 202 |
| Propylene | | 14632 | 17519 | 9758 | 11871 |
| Butylenes | | 4123 | 948 | 3105 | 980 |
| $C_5=$ | | 1274 | 292 | 1237 | 380 |
| $C_6=$ | | 356 | 79 | 305 | 46 |
| $CO + CO_2 + H_2$ | | 109 | 109 | 109 | 109 |
| Coke | | 515 | 750 | 1464 | 1636 |
| Total | 92843 | 92843 | 92843 | 92843 | 92843 |
| Weight Ratio: | | | | | |
| $(C_2 + C_3)/C_4$ plus | | 4.46 | 22.48 | 5.34 | 19.72 |

TABLE 2-continued

Material Balances for Maximum Ethylene and Maximum Propylene Cases

|  | Feed kg/hr | Case MP kg/hr | Case MPC kg/hr | Case ME kg/hr | Case MEC kg/hr |
|---|---|---|---|---|---|
| $C_4$ Plus/$C_3$= |  | 0.393 | .0753 | 0.476 | 0.118 |
| $C_2/C_3$ |  | 0.75 | 0.69 | 1.54 | 1.34 |

I claim:

1. A process for producing light olefins comprising:
   a) admixing a feedstream comprising an alcohol or an ether having 1 to 4 carbon atoms per molecule with a catalyst recirculation stream to provide a feedstream/recirculation stream;
   b) passing the feedstream/recirculation stream to a fluidized reaction zone containing an aluminophosphate molecular sieve catalyst in the presence of a diluent at effective conditions to produce a light olefin product stream comprising ethylene, propylene, and heavier olefins and a spent catalyst having a carbon deposit thereon;
   c) passing the light olefin product stream to a separation zone to produce an ethylene stream, a propylene stream, and a mixed $C_4$-plus stream;
   d) withdrawing a portion of the spent catalyst from the fluidized reaction zone and passing the portion of the spent catalyst to a regeneration zone and therein contacting the spent catalyst with an oxygen-containing stream at effective regeneration conditions to produce a regenerated catalyst comprising less than about 1 weight percent carbon;
   e) passing a feed admixture comprising at least a portion of the $C_4$-plus stream and at least a portion of the regenerated catalyst to a riser reactor in fluid communication with the fluidized reaction zone at effective cracking conditions to at least partially crack the feed admixture to produce a second product stream comprising additional amounts of ethylene and propylene and at least partially carbonizing the regenerated catalyst to provide a partially coked catalyst comprising from about 2 to about 30 weight percent carbon; and
   f) passing the second product stream and the partially coked catalyst to the fluidized reaction zone.

2. The process of claim 1 wherein the partially coked catalyst comprises between about 2 and about 10 weight percent carbon.

3. The process of claim 1 wherein the aluminophosphate catalyst comprises a SAPO catalyst.

4. The process of claim 3 wherein the SAPO catalyst comprises SAPO-17 or SAPO-34.

5. The process of claim 1 wherein the feed admixture comprises steam.

6. The process of claim 1 wherein the feed admixture comprises essentially all of the regenerated catalyst.

7. The process of claim 1 further comprising contacting a remaining portion of the spent catalyst with the feedstream in the riser.

* * * * *